US007060695B2

(12) United States Patent
Strong et al.

(10) Patent No.: US 7,060,695 B2
(45) Date of Patent: Jun. 13, 2006

(54) METHOD TO PREVENT VISION LOSS

(75) Inventors: H. Andrew Strong, North Vancouver (CA); Mohammad Azab, West Vancouver (CA); Troy Albert Reaves, Jr., Alpharetta, GA (US)

(73) Assignees: QLT, Inc., Vancouver (CA); Novartis AG, Basel (CH)

( * ) Notice: Subject to any disclaimer, the term of this patent is extended or adjusted under 35 U.S.C. 154(b) by 260 days.

(21) Appl. No.: 10/072,215

(22) Filed: Feb. 6, 2002

(65) Prior Publication Data

US 2002/0183302 A1 Dec. 5, 2002

Related U.S. Application Data

(60) Provisional application No. 60/266,961, filed on Feb. 6, 2001.

(51) Int. Cl.
*A61K 31/555* (2006.01)
(52) U.S. Cl. ........................ 514/185; 514/912
(58) Field of Classification Search ............... 514/185, 514/912, 392, 530, 573, 913
See application file for complete search history.

(56) References Cited

U.S. PATENT DOCUMENTS

| 5,198,460 A | 3/1993 | Pandey et al. ............ 514/410 |
| 5,798,349 A * | 8/1998 | Levy et al. ................. 514/185 |

FOREIGN PATENT DOCUMENTS

| WO | WO 02/062384 | 8/2002 |
| WO | WO 02/062386 | 8/2002 |

OTHER PUBLICATIONS

Michels, S. et al., "Changes in Neovascular Membranes and Normal Choroid Blood Vessels After Multiple Photodynamic Therapy Treatments!" Ophthalmologe 99(2):96-100 (2002).
Schmidt-Erfurth, U. et al., "Photodynamic Therapy with Verteporfin for Choroidal Neovascularization Caused by Age-Related Macular Degeneration: Results of Retreatmentsin a Phase 1 and 2 Study" Archives of Opthalmology 117(9):1177-1187 (1999).
Sickenberg, M. et al., "A Preliminary Study of Photodynamic Therapy Using Verteporfin for Choroidal Neovascularization in Pathologic Myopia Ocular Histoplasmosis Syndrome, Angioid Streaks, and Idiopathic Causes" Archives of Opthalmology 118(3):327-336 (2000).
Scott, L. et al., "Verteporfin." Drugs & Aging 16(2):139-148 (2000).
Treatment of Age-Related Macular Degeneration with Photodynamic Therapy (TAP) Study Group. "Photodynamic Therapy of Subfoveal Choroidal Neovascularization in Age-Related Macular Degeneration with Verteporfin" Arch. Opthalmol. 117: 1329-1345 (1999).

* cited by examiner

*Primary Examiner*—Zohreh Fay
(74) *Attorney, Agent, or Firm*—Morrison & Foerster LLP

(57) ABSTRACT

An improved method to treat conditions of the eye characterized by ocular neovascularization is provided in which patients are given and initial photodynamic therapy (PDT) treatment to destroy the neovasculature, and then are re-evaluated at least twice during the following 6 months, and retreated as necessary. Preferably, three retreatments are provided.

23 Claims, 3 Drawing Sheets

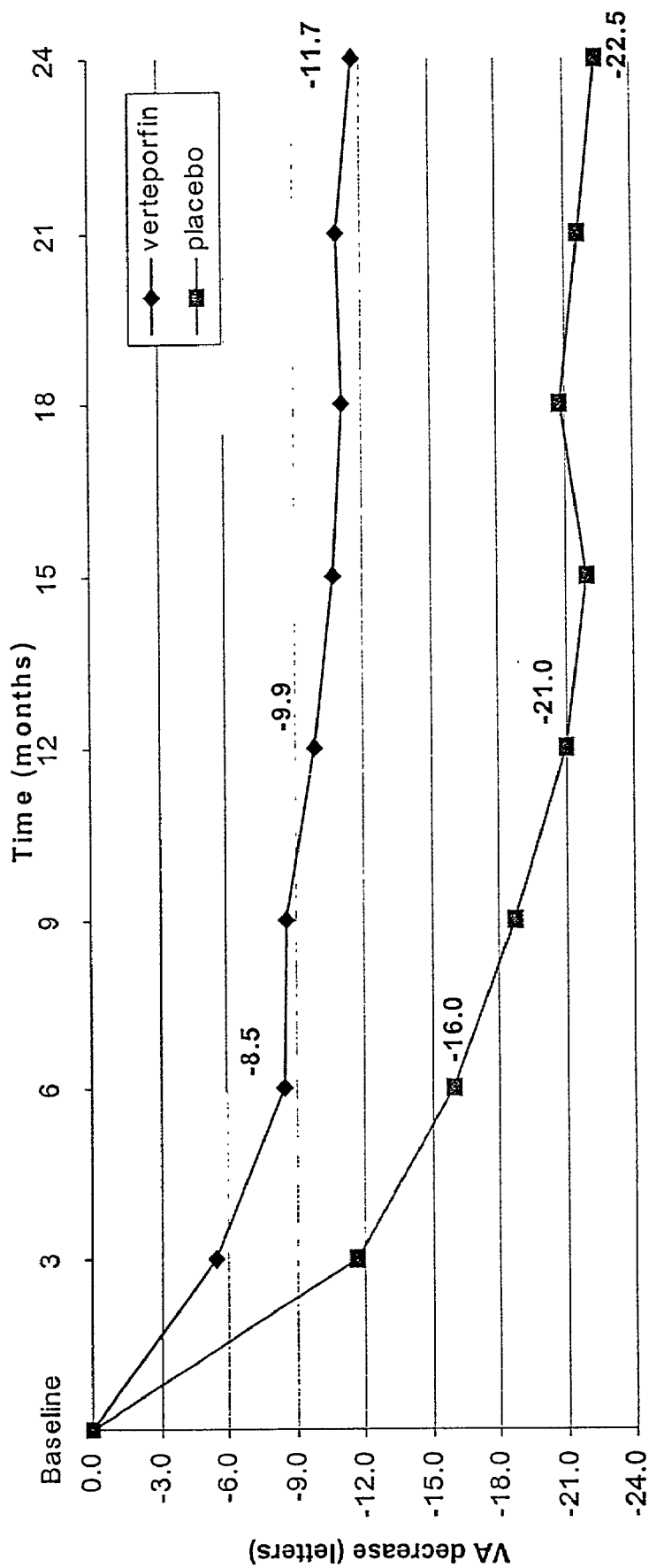
Figure 3: Mean change from baseline in visual acuity scores over time

METHOD TO PREVENT VISION LOSS

This application claims benefit of priority from U.S. Provisional Patent Application No. 60/266,961 filed Feb. 6, 2001, which is hereby incorporated by reference as if fully set forth.

TECHNICAL FIELD

The invention relates to an improved method of administering photodynamic therapy to treat conditions of the eye associated with unwanted neovascularization.

BACKGROUND OF THE INVENTION

Choroidal neovascularization leads to hemorrhage and fibrosis, with resultant visual loss in a number of eye diseases, including age-related macular degeneration (AMD), ocular histoplasmosis syndrome, pathologic myopia and certain inflammatory diseases. Similarly, corneal and retinal neovascularization are involved in other eye diseases leading to vision loss.

AMD causes severe, irreversible vision loss and is the leading cause of blindness in individuals older than 50 years in the Western World. Most patients have the non-neovascular ("dry") form, characterized by drusen and atrophic changes in the retinal pigment epithelium (RPE). Eighty to ninety percent of the severe vision loss due to AMD, however, is attributable to the form characterized by choroidal neovascularization (CNV), also called neovascular AMD. In the United States, between 70,000–200,000 individuals over the age of 65 develop the wet form of AMD every year. In CNV, the newly formed vessels have a tendency to leak blood and fluid, causing symptoms of scotoma and metamorphopsia. The new vessels are accompanied by proliferation of fibrous tissue. This complex of new vessels and fibrous tissue can destroy photoreceptors within 3 to 24 months. At the same time that existing CNV is destroying retinal tissue where it has formed, the lesion can continue to grow throughout the macula, resulting in progressive, severe and irreversible vision loss. Without treatment, most affected eyes will have poor central vision ($\leq 20/200$) within 2 years. In addition, when one eye of an individual develops CNV, the fellow eye has about a 50% chance of developing a similar CNV within 5 years.

Until recently, laser photocoagulation was the only treatment option available for CNV. Laser photocoagulation is limited to selected cases because the treatment destroys any viable photoreceptors overlying the area affected by CNV, often resulting in immediate visual acuity loss, especially when the lesion is subfoveal and the visual acuity is better than 20/200. For this reason, laser photocoagulation is only indicated for well-demarcated extrafoveal and juxtafoveal CNV as well as small, well-demarcated subfoveal lesions that have a pattern of classic CNV on fluorescein angiography. Recurrences following standard laser treatment of AMD cases occur in approximately 50% of cases. The recurrent CNV can lead to further vision loss, especially when the originally treated lesion was extrafoveal or juxtafoveal.

Photodynamic therapy (PDT) offers an alternative approach to selectively destroy CNV without significant destruction of overlying retina tissue, possibly by occluding the new vessels within the CNV. Photodynamic therapy is a two-step process consisting of an intravenous injection of a photosensitive compound (light-activated drug) followed by light application. The light sources used are non-thermal lasers or light emitting diodes (LEDs). The photosensitive compound preferentially accumulates in neovascular tissues, including the endothelial cells of choroidal neovascularization. In combination with localized light administration, this allows for selective treatment of the pathologic tissue. After exposure to light at a wavelength absorbed by the photosensitive compound, an energy transfer cascade is initiated, culminating in the formation of singlet oxygen which generates intracellular free radicals). These free radicals can disrupt cellular structures such as the cell membrane, mitochondria, and lysosomal membranes.

Occlusion of the neovasculature is presumed to be the major mechanism of PDT with verteporfin. Occlusion can occur through free radical damage to the endothelial cells, causing subsequent platelet adhesion and degranulation, and thrombus formation. A reduction in blood flow from the new vessels may lead to a confinement in the growth of the fibrovascular portion of the CNV with subsequent reduced risk of further vision loss.

Photodynamic therapy of neovascular conditions in the eye has been attempted over the past several years using various photosensitive compounds, e.g. porphyrin derivatives, such as hematoporphyrin derivative and porfimer sodium (PHOTOFRIN® Axcan Pharmaceuticals), phthalocyanines, green porphyrins (such as verteporfin, also known as BPD-MA), purpurins, such as tin ethyl etiopurpurin and texaphyrins, such as motexafin lutetium. The photosensitive compound verteporfin (Visudyne™, Novartis Ophthalmics) is the only photosensitive compound to have received regulatory approval for an ocular neovascular indication, and is now widely used for the treatment of AMD in patients with predominantly classic subfoveal CNV.

The approved protocol for treatment of CNV with verteporfin PDT (more fully described below) includes re-treatment of subjects as frequently as every three months if CNV leakage is detected upon fluorescein angiography. Although verteporfin PDT using this protocol closes neovasculature and prevents loss of visual acuity compared to placebo controls, in many subjects, there is still a decline in visual acuity from the baseline level following the initial treatment (Arch. Opthalmol. 117: 1329–1345). Although the dose ranges that are effective in humans were predicted using animal models (see for example, U.S. Pat. No. 5,798,349) it has been very difficult to optimize the treatment protocol in humans, so that the maximum benefit in the therapy can be achieved Consequently, there is a need for improving the PDT treatment of CNV and other neovascular conditions so that more visual acuity is preserved following the initial treatment.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

DISCLOSURE OF THE INVENTION

The invention is directed to a method to decrease the loss of vision that occurs in subjects being treated for ocular neovascularization using photodynamic treatment methods. The established protocol for PDT to treat ocular neovascularization in human subjects provides for an initial treatment, and subsequent retreatments up to every 3 months if angiographic evaluation shows leakage from the neovasculature. This allows for a single re-treatment before the 6 month evaluation and treatment. For example, a patient might be treated at 0, 3 and 6 months.

In one study (Schmidt-Erfurth et al. (1999) Arch Ophthalmol 117: 1177–187) the effect of providing up to two PDT retreatments during a 12 week period following the initial treatment was examined. No additional PDT treatments were provided. Although the study demonstrated that providing two retreatments with PDT was safe, no long term benefit on preservation of visual acuity was noted. The study suggested that a single treatment might control growth and prevent progression or growth of CNV beyond the area of CNV noted before treatment for as long as 3 months. Thus the treatment regimen based upon re-treatment every 3 months was adopted. However, based upon an examination of data from large numbers of patients treated with this regimen, the present inventors have discovered that although PDT treated patients suffer less visual acuity loss than those given placebo, there is still a significant loss in visual acuity during the 6 month period following the initial treatment (see FIG. 3). This decline in visual acuity persists at least until 24 months following the initial treatment.

The present invention is directed to increasing the frequency of additional PDT treatments during the period of about 6 months following the initial PDT treatment. This results in the visual acuity of patients being preserved to a greater extent than in comparison to using the established protocol in which patients are only evaluated and treated every three months.

Thus, and in one aspect, the invention is directed to a method of decreasing vision loss in subjects having ocular neovascularization, which comprises the steps of (1) providing an initial treatment comprising the steps of (a) administering to a subject having a neovascular lesion in the eye an amount of a formulation of a photoactive compound sufficient to permit an effective amount to localize in the neovascular lesion of said subject, (b) permitting sufficient time to elapse to allow an effective amount of said photoactive compound to localize in the neovascular lesion; and (c) irradiating the neovascular lesion with light absorbed by the photoactive compound, and (2) evaluating the patient angiographically for evidence of neovascular leakage at least twice within the period of about 6 months following the initial PDT treatment, and, if the evaluation indicates that neovascular leakage has occurred, providing a re-treatment to the patient, which is approximately identical to the initial PDT treatment. Preferably, the first reevaluation and re-treatment is carried out at about 1.5 months following the initial PDT treatment.

The above may be summarized as a method of decreasing vision loss in subjects having ocular neovascularization by providing, within a period of about six months following an initial PDT treatment, at least two PDT re-treatments following evaluations for neovascular leakage. Preferably, the first of the at least two evaluations is conducted at about 90 days following the initial PDT treatment. The above may also be stated as providing at least two PDT treatments in addition to the treatment at about 6 months following an initial PDT treatment.

The invention thus provides an improvement on the established protocol for PDT treatment of ocular neovasculature (which is treatment at about 3 months and about 6 months following an initial treatment) by introducing at least one additional PDT treatment, following a determination of neovascular leakage by angiography, between the initial treatment and the treatment at about 6 months.

In another embodiment, three treatments are provided, preferably at approximately 1.5 month intervals after the first PDT treatment but before the treatment at about 6 months. Stated differently, evaluation and re-treatment is carried out at about 1.5 months, about 3.0 months, and about 4.5 months following the initial PDT treatment and before the treatment at about 6 months. In yet another embodiment, reevaluations and re-treatments are carried out at 1 month intervals, at about 1, 2, 3, 4 and 5 months, for a total of five re-treatments within the period of about 6 months before the treatment that occurs at about 6 months in the established protocol. More frequent re-treatments are also within the scope of the present invention. Retreatments can be carried out with the same photoactive compound as the first treatment, or another photoactive compound, or a mixture of photoactive compounds.

After the 6 month period post the first PDT treatment, the subject may continue to be re-evaluated and/or re-treated with PDT.

DESCRIPTION OF THE DRAWINGS

FIG. 3 is a graph showing the loss of visual acuity of patients receiving PDT with verteporfin compared to the loss of visual acuity of patients receiving placebo.

MODES OF CARRYING OUT THE INVENTION

Figure 1A:
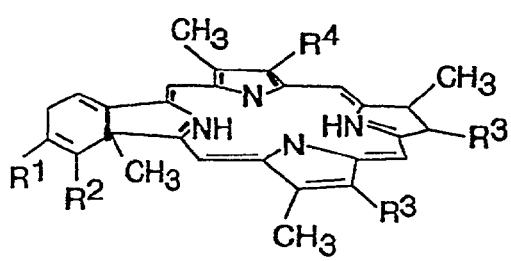
FIG. 1 is a drawing of preferred forms of the green porphyrins useful in the methods of the invention.
Figure 1B:
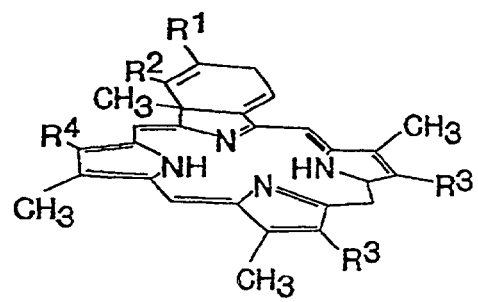

In the general approach that forms the subject matter of the invention, a human subject who has been diagnosed with ocular neovascularization is administered a suitable photoactive compound in an amount known in the art as sufficient to provide an effective concentration of the photoactive compound in the eye. After a suitable time period known in the art to permit an effective concentration of the compound to accumulate in the desired region of the eye, this region is irradiated with light absorbed by the photoactive compound. The irradiation results in excitation of the compound which, in turn, results in closure of neovasculature, and cessation of leakage. The patient is reevaluated for evidence of recurring neovascular leakage at least twice within a period of 6 months of the first treatment (and in addition to the treatment at about 6 months in the established protocol), and if neovascular leakage has occurred, the patient is retreated. In preferred embodiments of the invention, the procedure is repeated at least twice, more preferably three times, within before treatment at about 6 months from the first treatment.

The invention provides an improvement on the established protocol for PDT treatment of ocular neovasculature by providing more frequent PDT treatments during the first six months following an initial PDT treatment. The established protocol is for treatment at a frequency of only about every 90 days. The increased frequency of PDT treatments, as provided by the present invention, may be at intervals of 60 or about 60 days (or two months), 45 or about 45 days (or about 1.5 month), 30 or about 30 days (about one month), or 15 or about 15 days (or about 2 weeks) following the initial PDT treatment and for the duration of a 6 month period following an initial treatment. Treatment intervals of less than 15 or about 15 days, such as, but not limited to 10 or about 10 days, or 7 or about 7 days, during the first 6 months after an initial PDT treatment may also be used with the present invention.

Benefits provided by the present invention include, but are not limited to, a greater degree of closure of neovasculature, improved visual acuity, and/or the advantage of avoiding increases in retinal pigment epithelium (RPE) atrophy and additive damage to the RPE.

While the increased frequency of treatment may also be viewed as an increased frequency of angiographic evaluation for neovasculature leakage, it is not the evaluation that produces a beneficial preservation of visual acuity in comparison to the established protocol. Instead, it is the increased frequency of treatment during the first six months that results in a decreased loss of visual acuity. This beneficial decrease in the loss of acuity may be characterized as a decrease in the initial loss of acuity during the first three or six months after an initial treatment and/or a decrease in the overall loss of acuity during the first 24 months under treatment.

In a preferred embodiment of the invention, the methods disclosed herein are applied to the treatment of choroidal neovasculature (CNV) in a subject afflicted with the condition. The subject may be previously diagnosed as having AMD, and may have undergone other treatment protocols for the condition.

While a preferred embodiment of the invention is the use of the same photoactive compound (or combination of photoactive compounds) as that used in the initial PDT treatment, use of a different photoactive compound (or combination of photoactive compounds) in the more frequent treatments during the first 6 months following the initial treatment is also within the scope of the invention. Stated differently, the photoactive compound(s) used in the treatments of the invention between the initial PDT treatment and the treatment at about 6 months after the initial treatment may be the same or different from those used in the initial treatment.

The present invention also provides for the use of one or more photoactive compound in the preparation or formulation of a medicament for use in the methods of the invention. The improved photodynamic therapy (PDT) methods according to the invention can be performed using any of a number of photoactive compounds (or photosensitizers). For example, various derivatives of hematoporphyrin have been described, including improvements on hematoporphyrin derivative per se such as those described in U.S. Pat. Nos. 5,028,621; 4,866,168; 4,649,151; and 5,438,071, the entire contents of which are incorporated herein by reference as if fully set forth. In addition, pheophorbides are described in U.S. Pat. Nos. 5,198,460; 5,002,962; and 5,093,349; bacteriochlorins in U.S. Pat. Nos. 5,171,741 and 5,173,504; and dimers and trimers of hematoporphyrins in U.S. Pat. Nos. 4,968,715 and 5,190,966. The contents of these patents are also incorporated herein by reference. In addition, U.S. Pat. No. 5,079,262 describes the use of a precursor to hematoporphyrin, aminolevulinic acid (ALA), as the source of a photoactive compound. The use of phthalocyanine photosensitive compounds in photodynamic therapy is described in U.S. Pat. No. 5,166,197. The contents of all of the foregoing patents are incorporated herein by reference. Other possible photoactive compounds include purpurins (such as tin-ethyl etiopurpurin), merocyanines, iminochlorinaspartic acid derivative (U.S. Pat. No. 6,063,777), texaphyrins (such as motexafin lutetium) and porphycenes. Particular preferred photoactive compounds for use in the invention method are the green porphyrins. These porphyrins are described in U.S. Pat. Nos. 4,883,790; 4,920,143; 5,095,030; and 5,171,749, the entire contents of which are incorporated herein by reference. As these photoactive agents represent a particularly preferred embodiment, typical formulas for these compounds are represented herein in FIG. 1.

Referring to FIG. 1, in preferred embodiments, each of $R^1$ and $R^2$ is independently selected from the group consisting of carbalkoxyl (2–6C), alkyl (1–6C), arylsulfonyl (6–10C), cyano and —$CONR^5CO$ wherein $R^5$ is aryl (6–10C) or alkyl (1–6C); each $R^3$ is independently carboxyl, carboxyalkyl (2–6C) or a salt, amide, ester or acylhydrazone thereof or is alkyl (1–6C); $R^4$ is $CH=CH_2$ or —$CH(OR^{4'})CH_3$ wherein $R^{4'}$ is H, or alkyl (1–6C) optionally substituted with a hydrophilic substituent. Especially preferred also are green porphyrins of the formula shown in FIG. 1C or 1D or mixtures thereof.

Figure 1C:
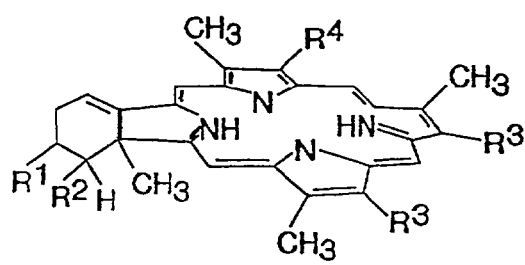
Figure 1D:
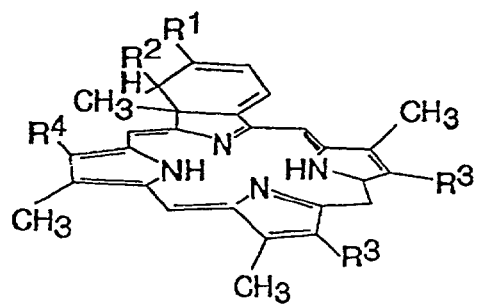
Figure 1E:
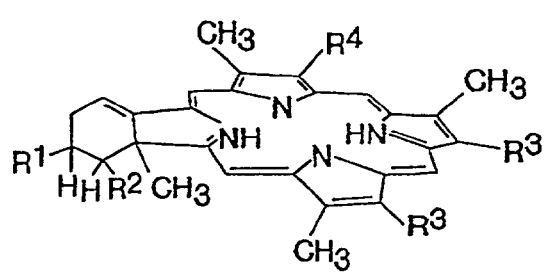
Figure 1F:
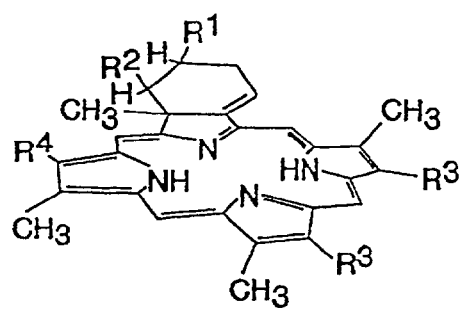
Figure 2:
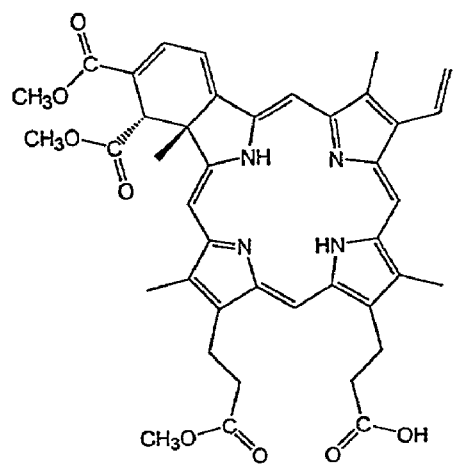
FIG. 2 is a drawing of the chemical structure of verteporfin.
Figure 2:
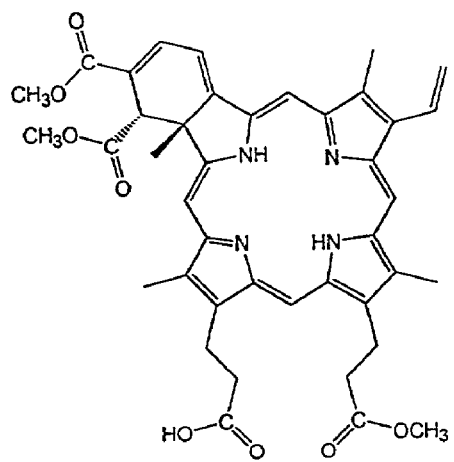

More preferred are embodiments are those wherein the green porphyrin is of the formula shown in FIG. 1C or 1D or a mixture thereof and wherein each of $R^1$ and $R^2$ is independently carbalkoxyl (2–6C); one $R^3$ is carboxyalkyl (2–6C) and the other $R^3$ is an ester of a carboxyalkyl (2–6C) substituent; and $R^4$ is $CH=CH_2$ or —$CH(OH)CH_3$.

Still more preferred are embodiments wherein green porphyrin is of the formula shown in FIG. 1C and wherein $R^1$ and $R^2$ are methoxycarbonyl; one $R^3$ is —$CH_2CH_2COOCH_3$ and the other $R^3$ is $CH_2CH_2COOH$; and $R^44$ is $CH=CH_2$; i.e., BPD-MA.

Particularly preferred green porphyrins for the practice of the invention are compounds such as BPD-DA, -DB, -MA, and -MB, and in particular BPD-MA, EA6, and B3. These compounds are porphyrin derivatives obtained by reacting a porphyrin nucleus with an alkyne in a Diels-Alder type reaction to obtain a monohydrobenzoporphyrin as described in U.S. Pat. No. 5,171,749, which is hereby incorporated in its entirety by reference. Other photosensitizers that may be used in the present invention include those described in U.S. Pat. Nos. 5,308,608, 6,093,739, 5,703,230, 5,831,088, 5,726,304, and 5,405,957.

It is preferred that the absorption spectrum of the photoactive compound be in the visible range, typically between 350 nm and 1200 nm, more preferably between 400–900 nm, and even more preferably between 600–900 nm. Generally, any polypyrrolic macrocyclic photoactive compound may be used in the practice of the invention.

Representations of BPD-MA$_C$ and BPD-MA$_D$, which are the components of Verteporfin, as well as illustrations of A and B ring forms of EA6 and B3, are as follows:

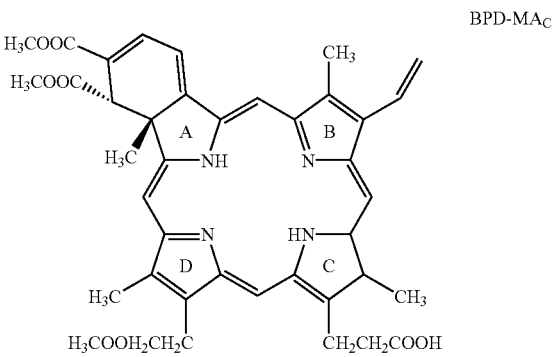

BPD-MA$_C$

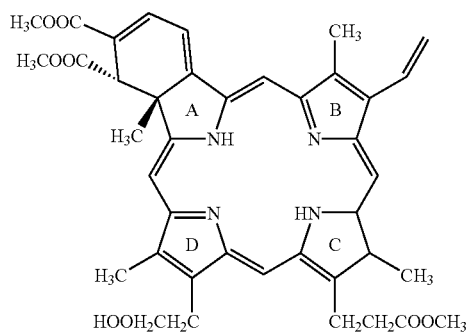

BPD-MA$_D$

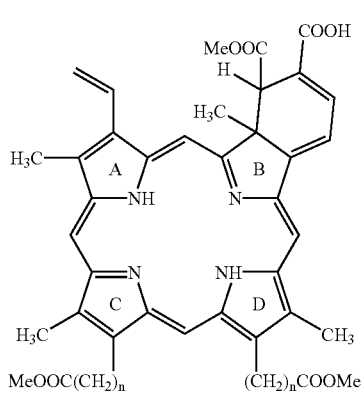

B-B3

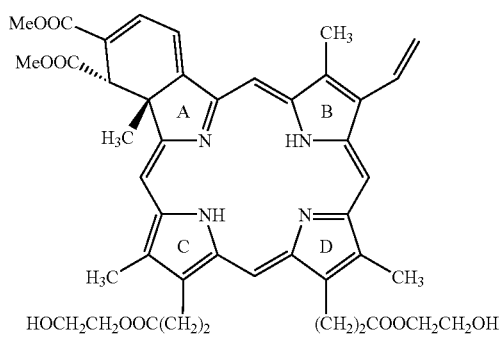

A-EA6

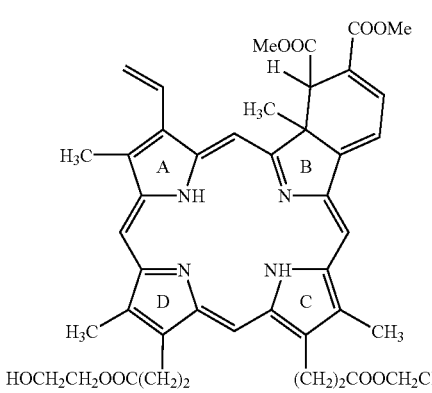

B-EA6

A-B3

Further examples of other photosensitizers for use in the present invention include, but are not limited to, angelicins, some biological macromolecules such as lipofuscin; photosystem II reaction centers; and D1-D2-cyt b-559 photosystem II reaction centers, chalcogenapyrillium dyes, chlorins, chlorophylls, coumarins, cyanines, ceratin DNA and related compounds such as adenosine; cytosine; 2'-deoxyguanosine-5'-monophosphate; deoxyribonucleic acid; guanine; 4-thiouridine; 2'-thymidine 5'-monophosphate; thymidylyl (3'-5')-2'-deoxyadenosine; thymidylyl(3'-5')-2'-deoxyguanosine; thymine; and uracil, certain drugs such as adriamycin; afloqualone; amodiaquine dihydrochloride; chloroquine diphosphate; chlorpromazine hydrochloride; daunomycin; daunomycinone; 5-iminodaunomycin; doxycycline; furosemide; gilvocarcin M; gilvocarcin V; hydroxychloroquine sulfate; lumidoxycycline; mefloquine hydrochloride; mequitazine; merbromin (mercurochrome); primaquine diphosphate; quinacrine dihydrochloride; quinine sulfate; and tetracycline hydrochloride, certain flavins and related compounds such as alloxazine; flavin mononucleotide; 3-hydroxyflavone; limichrome; limiflavin; 6-methylalloxazine; 7-methylalloxazine; 8-methylalloxazine; 9-methylalloxazine; 1-methyl limichrome; methyl-2-methoxybenzoate; 5-nitrosalicyclic acid; proflavine; and riboflavin, fullerenes, metalloporphyrins, metallophthalocyanines, methylene blue derivatives, naphthalimides, naphthalocyanines, certain natural compounds such as bis(4-hydroxy-3-methoxyphenyl)-1,6-heptadiene-3,5-dione; 4-(4-hydroxy-3-methoxyphenyl)-3-buten-2-one; N-formylkynurenine; kynurenic acid; kynurenine; 3-hydroxykynurenine; DL-3-hydroxykynurenine; sanguinarine; berberine; carmane; and 5,7,9(11),22-ergostatetraene-3 β-ol, nile blue derivatives, NSAIDs (nonsteroidal anti-inflammatory drugs), perylenequinones, phenols, pheophorbides, pheophytins, photosensitizer dimers and conjugates, phthalocyanines, porphycenes, porphyrins, psoralens, purpurins, quinones, retinoids, rhodamines, thiophenes, verdins, vitamins and xanthene dyes (Redmond and Gamlin, *Photochem. Photobiol.*, 70(4):391–475 (1999)).

Exemplary angelicins include 3-aceto-angelicin; angelicin; 3,4'-dimethyl angelicin; 4,4'-dimethyl angelicin; 4,5'-dimethyl angelicin; 6,4'-dimethyl angelicin; 6,4-dimethyl angelicin; 4,4',5'-trimethyl angelicin; 4,4',5'-trimethyl-1'-thioangelicin; 4,6,4'-trimethyl-1'-thioangelicin; 4,6,4'-trimethyl angelicin; 4,6,5'-trimethyl-1'-thioangelicin; 6,4,4'-trimethyl angelicin; 6,4',5'-trimethyl angelicin; 4,6,4',5'-tetramethyl-1'-thioangelicin; and 4,6,4',5'-tetramethyl angelicin.

Exemplary chalcogenapyrillium dyes include pyrilium perchlorate, 4,4'-(1,3-propenyl)-bis[2,6-di(1,1-dimethyl-ethyl)]-; pyrilium perchlorate, 2,6-bis(1,1-dimethyl-ethyl)-4-[1-[2,6-bis(1,1-dimethyl-ethyl)selenopyran-4-ylidene]-3-propenyl-; pyrilium hexofluoro phosphate, 2,6-bis-(1,1-dimethyl-ethyl)-selenopyran-4-ylidene]-3-propenyl-; pyrilium hexofluoro phosphate, 2,6-bis(1,1-dimethyl-ethyl)-selenopyran-4-ylidene]-3-propenyl-; pyrilium perchlorate, 2,6-bis(1,1-dimethyl-ethyl)-4-[1-[2,6-bis(1,1-dimethyl-ethyl)telluropyran-4-ylidene]-3-propenyl-; pyrilium hexofluoro phosphate, 2,6-bis(1,1-dimethyl-ethyl)-4-[1-[2,6-bis(1,1-dimethyl-ethyl)telluropyran-4-ylidene]-3-propenyl-; pyrilium perchlorate, 2,6-bis(1,1-dimethyl-ethyl)-4-[1-[2,6-bis(1,1-dimethyl-ethyl)thiapyran-4-ylidene]-3-propenyl]-; selenopyrilium hexofluoro phosphate, 2,6-bis(1,1-dimethyl-ethyl)-4-[1-[2,6-bis(1,1-dimethyl-ethyl)selenopyran-4-ylidene]-3-propenyl]-; selenopyrilium, 2,6-bis(1,1-dimethylethyl)-4-[1-[2,6-bis(1,1-dimethylethyl)selenopyran-4-ylidene]-3-propenyl]-; selenopyrilium percheorate, 2,6-bis(1,1-dimethyl-ethyl)-4-[1-[2,6-bis(1,1-dimethyl-ethyl)-4-[1-[2,6-bis(1,1-dimethyl-ethyl)telluropyran-4-ylidene]-3-propenyl]-; selenopyrilium hexofluoro phosphate, 2,6-bis(1,1-dimethyl-ethyl)-4-[1-[2,6-bis(1,1-dimethyl-ethyl)telluropyran-4-ylidene]-3-propenyl]-; selenopyrilium hexofluoro phosphate, 2,6-bis(1,1-dimethyl-ethyl)-4-[2-[2,6-bis(1,1-dimethyl-ethyl)selenopyran-4-ylidene]-4-(2-butenyl)]-; selenopyrilium hexofluoro phosphate, 2,6-bis(1,1-dimethyl-ethyl)-4-[2-[2,6-bis(1,1-dimethyl-ethyl)selenopyran-4-ylidene]-4-(2-pentenyl)]-; telluropyrilium tetrafluoroborate, 2,6-bis(1,1-dimethylethyl)-4-[1-[2,6-bis(1,1-dimethyl-ethyl)-telluropyran-4-ylidene]-3-propenyl]-; telluropyrilium hexofluoro phosphate, 2,6-bis(1,1-dimethyl-ethyl)-4-[1-[2,6-bis(1,1-dimethyl-ethyl)telluropyran-4-ylidene]-3-propenyl]-; telluropyrilium hexofluoro phosphate, 2,6-bis(1,1-dimethyl-ethyl)-4-[1-[2,6-bis(1,1-dimethyl-ethyl)telluropyran-4-ylidene]ethyl-; telluropyrilium hexofluoro phosphate, 2,6-bis(1,1-dimethyl-ethyl)-4-[1-[2,6-bis(1,1-dimethyl-ethyl)-telluropyran-4-ylidene]methyl-; thiopyrilium hexofluoro phosphate, 2,6-bis(1,1-dimethyl-ethyl)-4-[1-[2,6-bis(1,1-dimethyl-ethyl)thiopyran-4-ylidene]-3-propenyl]-; thiopyrilium hexofluoro phosphate, 2,6-bis(1,1-dimethyl-ethyl)-4-[1-[2,6-bis(1,1-dimethyl-ethyl)selenopyran-4-ylidene]-3-propenyl]-; and thiopyrilium hexofluoro phosphate, 2,6-bis(1,1-dimethyl-ethyl)-4-[1-[2,6-bis(1,1-dimethyl-ethyl)telluropyran-4-ylidene]-3-propenyl]-.

Exemplary chlorins dyes include 5-azachlorin dimethyl ester derivative; 5,10,15,20-tetrakis-(m-hydroxyphenyl)bacteriochlorin; benzoporphyrin derivative monoacid ring A; benzoporphyrin derivative monoacid ring-A; porphine-2,18-dipropanoic acid, 7-[2-dimethyl-amino)-2-oxoethyl]-8-ethylidene-7,8-dihydro-3,7,12,17-tetramethyl, dimethylester; porphine-2,18-dipropanoic acid, 7-[2-dimethyl-amino)-2-oxoethyl]-8-ethylidene-8-ethyl-7,8-dihydro-3,7,12,17-tetramethyl, dimethylester Z; porphine-2,18-dipropanoic acid, 7-[2-dimethyl-amino)-2-oxoethyl]-8-ethylidene-8-ethyl-7,8-dihydro -3,7,12,17-tetramethyl, dimethylester Z ECHL; porphine-2,18-dipropanoic acid, 7-[2-dimethyl-amino)-2-oxoethyl]-8-ethylidene-8-n-heptyl-7,8-dihydro-3,7,12,17-tetramethyl, dimethylester Z; tin (II) porphine-2,18-dipropanoic acid, 7-[2-(dimethylamino-2-oxoethyl]-8-ethylidene-8-n-heptyl-7,8-dihydro-3,7,12,17-tetramethyl, dimethylester Z; chlorin $e_6$; chlorin $e_6$ dimethyl ester; chlorin $e_6$ $k_3$; chlorin $e_6$ monomethyl ester; chlorin $e_6$ $Na_3$; chlorin $p_6$; chlorin $p_6$-trimethylester; chlorin derivative zinc (II) porphine-2,18-dipropanoic acid, 7-[2-(dimethylamino)-2-oxoethyl]-8-ethylidene-8-n-heptyl-7,8-dihydro-3,7,12,17-tetramethyl, dimethylester Z; $13^1$-deoxy-20-formyl-vic-dihydroxy-bacteriochlorin di-tert-butyl aspartate; $13^1$-deoxy-20-formyl-4-keto-bacteriochlorin di-tert-butyl aspartate; di-L-aspartyl chlorin $e_6$; mesochlorin; 5,10,15,20-tetrakis-(m-hydroxyphenyl) chlorin; meta-(tetrahydroxyphenyl)chlorin; methyl-$13^1$-deoxy-20-formyl-4-keto-bacteriochlorin; mono-L-aspartyl chlorin $e_6$; photoprotoporphyrin IX dimethyl ester; phycocyanobilin dimethyl ester; protochlorophyllide a; tin (IV) chlorin $e_6$; tin chlorin $e_6$; tin L-aspartyl chlorin $e_6$; tin octaethyl-benzochlorin; tin (IV) chlorin; zinc chlorin $e_6$; and zinc L-aspartyl chlorin $e_6$.

Exemplary chlorophylls dyes include chlorophyll a; chlorophyll b; oil soluble chlorophyll; bacteriochlorophyll a; bacteriochlorophyll b; bacteriochlorophyll c; bacteriochlorophyll d; protochlorophyll; protochlorophyll a; amphiphilic chlorophyll derivative 1; and amphiphilic chlorophyll derivative 2.

Exemplary coumarins include 3-benzoyl-7-methoxycoumarin; 7-diethylamino-3-thenoylcoumarin; 5,7-dimethoxy-3-(1-naphthoyl) coumarin; 6-methylcoumarin; 2H-selenolo[3,2-g] [1] benzopyran-2-one; 2H-selenolo[3,2-g] [1] benzothiopyran-2-one; 7H-selenolo[3,2-g] [1] benzoselenopyran-7-one; 7H-selenopyrano[3,2-f] [1] benzofuran-7-one; 7H-selenopyrano[3,2-f] [1] benzo-thiophene-7-one; 2H-thienol[3,2-g] [1] benzopyran-2-one; 7H-thienol[3,2-g] [1] benzothiopyran-7-one; 7H-thiopyrano[3,2-f] [1] benzofuran-7-one; coal tar mixture; khellin; RG 708; RG277; and visnagin.

Exemplary cyanines include benzoselenazole dye; benzoxazole dye; 1,1'-diethyloxacarbocyanine; 1,1'-diethyloxadicarbocyanine; 1,1'-diethylthiacarbocyanine; 3,3'-dialkylthiacarbocyanines (n=2–18); 3,3'-diethylthiacarbocyanine iodide; 3,3'-dihexylselenacarbocyanine; kryptocyanine; MC540 benzoxazole derivative; MC540 quinoline derivative; merocyanine 540; and meso-ethyl, 3,3'-dihexylselenacarbocyanine.

Exemplary fullerenes include $C_{60}$; $C_{70}$; $C_{76}$; dihydrofullerene; 1,9-(4-hydroxycyclohexano)-buckminster-fullerene; [1-methyl-succinate-4-methyl-cyclohexadiene-2,3]-buckminster-fullerene; and tetrahydro fullerene.

Exemplary metalloporphyrins include cadmium (II) chlorotexaphyrin nitrate; cadmium (II) meso-diphenyl tetrabenzoporphyrin; cadmium meso-tetra-(4-N-methylpyridyl)-porphine; cadmium (II) texaphyrin; cadmium (II) texaphyrin nitrate; cobalt meso-tetra-(4-N-methylpyridyl)-porphine; cobalt (II) meso(4-sulfonatophenyl)-porphine; copper hematoporphyrin; copper meso-tetra-(4-N-methylpyridyl)-porphine; copper (II) meso(4-sulfonatophenyl)-porphine; Europium (III) dimethyltexaphyrin dihydroxide; gallium tetraphenylporphyrin; iron meso-tetra(4-N-methylpyridyl)-porphine; lutetium (III) tetra(N-methyl-3-pyridyl)-porphyrin chloride; magnesium (II) meso-diphenyl tetrabenzoporphyrin; magnesium tetrabenzoporphyrin; magnesium tetraphenylporphyrin; magnesium (II) meso(4-sulfonatophenyl)-porphine; magnesium (II) texaphyrin hydroxide metalloporphyrin; magnesium meso-tetra-(4-N-methylpyridyl)-porphine; manganese meso-tetra-(4-N-methylpyridyl)-porphine; nickel meso-tetra(4-N-methylpyridyl)-porphine; nickel (II) meso-tetra(4-sulfonatophenyl)-porphine; palladium (II) meso-tetra-(4-N-methylpyridyl)-porphine; palladium meso-tetra-(4-N-methylpyridyl)-porphine; palladium tetraphenylporphyrin; palladium (II) meso(4-sulfonatophenyl)-porphine; platinum (II) meso(4-sulfonatophenyl)-porphine; samarium (II) dimethyltexaphyrin dihydroxide; silver (II) meso(4-sulfonatophenyl)-porphine; tin (IV) protoporphyrin; tin mesotetra-(4-N-methylpyridyl)-porphine; tin meso-tetra(4-sulfonatophenyl)-porphine; tin (IV) tetrakis(4-sulfonatophenyl) porphyrin dichloride; zinc (II) 15-aza-3,7,12,18-tetramethyl-porphyrinato-13,17-diyl-dipropionic acid-dimethylester; zinc (II) chlorotexaphyrin chloride; zinc coproporphyrin III; zinc (II) 2,11,20,30-tetra-(1,1-dimethyl-ethyl)tetranaphtho(2,3-b:2',3'-g:2"3"-1:2'"3'"-q)porphyrazine; zinc (II) 2-(3-pyridyloxy)benzo[b]-10,19,28-tri(1,1-dimethylethyl)trinaphtho[2',3'-g:2"3"1::2",3'"-q] porphyrazine; zinc (II) 2,18-bis-(3-pyridyloxy)dibenzo[b,1]-10,26-di(1,1-dimethyl-ethyl)dinaphtho[2',3'-g:2'",3'"-q] porphyrazine; zinc (II) 2,9-bis-(3-pyridyloxy)dibenzo[b,g]-17,26-di(1,1-dimethyl-ethyl)dinaphtho[2",3"-1:2'",3'"-q] porphyrazine; zinc (II) 2,9,16-tris-(3-pyridyloxy) tribenzo [b,g,1]-24=(1,1-dimethyl-ethyl)naphtho[2'",3'"-q] porphyrazine; zinc (II) 2,3-bis-(3-pyridyloxy) benzo[b]-10,19,28-tri(1.1-dimethyl-ethyl)trinaphtho[2',3'-g:2",3"1:2'",3'"-q]porphyrazine; zinc (II) 2,3,18,19-tetrakis-(3-pyridyloxy) dibenzo[b,1]-10,26-di(1,1-dimethyl-ethyl)trinaphtho[2',3'-g:2'",3'"-q]porphyrazine; zinc (II) 2,3,9,10-tetrakis-(3-pyridyloxy) dibenzo[b,g]-17,26-di(1,1-dimethyl-ethyl)dinaphtho[2",3"-1:2'",3'"-q]porphyrazine; zinc (II) 2,3,9,10,16,17-hexakis-(3-pyridyloxy)tribenzo[b,g,1]-24-(1,1-dimethyl-ethyl)naphtho[2'",3'"-q]porphyrazine; zinc (II) 2-(3-N-methyl)pyridyloxy)benzo[b]-10,19,28-tri(1,1-dimethyl-ethyl)trinaphtho[2',3'-g:2",3"1:2'",3'"-q]porphyrazine monoiodide; zinc (II) 2,18-bis-(3-(N-methyl)pyridyloxy)dibenzo[b,1]-10,26-di(1,1-dimethylethyl)dinaphtho[2',3'-g:2'",3'"-q]porphyrazine diiodide; zinc (II) 2,9-bis-(3-(N-methyl)pyridyloxy)dibenzo[b,g]-17,26-di(1,1-dimethylethyl)dinaphtho[2",3"-1:2'",3'"-q]porphyrazine diiodide; zinc (II) 2,9,16-tris-(3-(N-methyl-pyridyloxy) tribenzo[b,g,1]-24-(1,1-dimethylethyl)naphtho[2'",3'"-q] porphyrazine triiodide; zinc (II) 2,3-bis-(3-(N-methyl)pyridyloxy)benzo[b]-10,19,28-tri(1,1-dimethylethyl) trinaphtho[2',3'-g:2",3"-1:2'",3'"-q]porphyrazine diiodide; zinc (II) 2,3,18,19-tetrakis-(3-(N-methyl)pyridyloxy)dibenzo[b,1]-10,26-di(1,1-dimethyl)dinaphtho[2',3'-g:2'",3'"-q]porphyrazine tetraiodide; zinc (II) 2,3,9,10-tetrakis-(3-(N-methyl)pyridyloxy)dibenzo[g,g]-17,26-di(1,1-dimethylethyl)dinaphtho[2",3"-1:2'",3'"-q]porphyrazine tetraiodide; zinc (II) 2,3,9,10,16,17-hexakis-(3-(N-methyl)pyridyloxy)tribenzo[b,g,1]-24-(1,1-dimethylethyl)naphtho[2'",3'"-q]porphyrazine hexaiodide; zinc (II) meso-diphenyl tetrabenzoporphyrin; zinc (II) meso-triphenyl tetrabenzoporphyrin; zinc (II) meso-tetrakis(2,6-dichloro-3-sulfonatophenyl) porphyrin; zinc (II) meso-tetra-(4-N-methylpyridyl)-porphine; zinc (II) 5,10,15,20-meso-tetra(4-octyl-phenylpropynyl)-porphine; zinc porphyrin c; zinc protoporphyrin; zinc protoporphyrin IX; zinc (II) meso-triphenyl-tetrabenzoporphyrin; zinc tetrabenzoporphyrin; zinc (II) tetrabenzoporphyrin; zinc tetranaphthaloporphyrin; zinc tetraphenylporphyrin; zinc (II) 5,10,15,20-tetraphenylporphyrin; zinc (II) meso (4-sulfonatophenyl)-porphine; and zinc (II) texaphyrin chloride.

Exemplary metallophthalocyanines include aluminum mono-(6-carboxy-pentyl-amino-sulfonyl)-trisulfo-phthalocyanine; aluminum di-(6-carboxy-pentyl-amino-sulfonyl)-trisulfophthalocyanine; aluminum (III) octa-n-butoxy phthalocyanine; aluminum phthalocyanine; aluminum (III) phthalocyanine disulfonate; aluminum phthalocyanine disulfonate; aluminum phthalocyanine disulfonate (cis isomer); aluminum phthalocyanine disulfonate (clinical prep.); aluminum phthalocyanine phthalimido-methyl sulfonate; aluminum phthalocyanine sulfonate; aluminum phthalocyanine trisulfonate; aluminum (III) phthalocyanine trisulfonate; aluminum (III) phthalocyanine tetrasulfonate; aluminum phthalocyanine tetrasulfonate; chloroaluminum phthalocyanine; chloroaluminum phthalocyanine sulfonate; chloroaluminum phthalocyanine disulfonate; chloroaluminum phthalocyanine tetrasulfonate; chloroaluminum-t-butyl-phthalocyanine; cobalt phthalocyanine sulfonate; copper phthalocyanine sulfonate; copper (II) tetra-carboxy-phthalocyanine; copper (II)-phthalocyanine; copper t-butyl-phthalocyanine; copper phthalocyanine sulfonate; copper (II) tetrakis-[methylene-thio[(dimethyl-amino)methylidyne]] phthalocyanine tetrachloride; dichlorosilicon phthalocyanine; gallium (III) octa-n-butoxy phthalocyanine; gallium (II) phthalocyanine disulfonate; gallium phthalocyanine disulfonate; gallium phthalocyanine tetrasulfonate-chloride; gallium (II) phthalocyanine tetrasulfonate; gallium phthalocyanine trisulfonate-chloride; gallium (II) phthalocyanine trisulfonate; $GaPcS_1tBu_3$; $GaPcS_2tBu_2$; $GaPcS_3tBu_1$; germanium (IV) octa-n-butoxy phthalocyanine; germanium phthalocyanine derivative; silicon phthalocyanine derivative; germanium (IV) phthalocyanine octakis-alkoxy-derivatives; iron phthalocyanine sulfonate; lead (II) 2,3,9,10,16,17,23,24-octakis(3,6-dioxaheptyloxy) phthalocyanine; magnesium t-butyl-phthalocyanine; nickel (II) 2,3,9,10,16,17,23,24-octakis(3,6-dioxaheptyloxy) phthalocyanine; palladium (II) octa-n-butoxy phthalocyanine; palladium (II) tetra(t-butyl)-phthalocyanine; (diol) (t-butyl)$_3$-phthalocyanato palladium(II); ruthenium(II) dipotassium[bis(triphenyl-phosphine-monosulphonate) phthalocyanine; silicon phthalocyanine bis(tri-n-hexyl-siloxy)-; silicon phthalocyanine bis(tri-phenyl-siloxy)-; $HOSiPcOSi(CH_3)_2(CH_2)_3N(CH_3)_2$; $HOSiPcOSi(CH_3)_2(CH_2)_3N(CH_2CH_3)_2$; $SiPc[OSi(CH_3)_2(CH_2)_3N(CH_3)_2]_2$; $SiPc[OSi(CH_3)_2(CH_2)_3N(CH_2CH_3)(CH_2)_2N(CH_3)_2]_2$; tin (IV) octa-n-butoxy phthalocyanine; vanadium phthalocyanine sulfonate; zinc (II) octa-n-butoxy phthalocyanine; zinc (II) 2,3,9,10,16,17,23,24-octakis(2-ethoxy-ethoxy) phthalocyanine; zinc (II) 2,3,9,10,16,17,23,24-octakis(3,6-dioxaheptyloxy) phthalocyanine; zinc (II) 1,4,8,11,15,18,22,25-octa-n-butoxy-phthalocyanine; zn(II)-phthalocyanine-octabutoxy; zn(II)-phthalocyanine; zinc phthalocyanine; zinc (II) phthalocyanine; zinc phthalocyanine and perdeuterated zinc phthalocyanine; zinc (II) phthalocyanine disulfonate; zinc phthalocyanine disulfonate; zinc phthalocyanine sulfonate; zinc phthalocyanine tetrabromo-; zinc (II) phthalocyanine tetra-t-butyl-; zinc (II) phthalocyanine tetra-(t-butyl)-; zinc phthalocyanine tetracarboxy-; zinc phthalocyanine tetrachloro-; zinc phthalocyanine tetrahydroxyl; zinc phthalocyanine tetraiodo-; zinc ((I) tetrakis-(1,1-dimethyl-2-phthalimido)ethyl phthalocyanine; zinc (II) tetrakis-(1,1-dimethyl-2-amino)-ethyl-phthalocyanine; zinc (II) phthalocyanine tetrakis(1,1-dimethyl-2-trimethyl ammonium)ethyl tetraiodide; zinc phthalocyanine tetrasulphonate; zinc phthalocyanine tetrasulfonate; zinc (II) phthalocyanine tetrasulfonate; zinc (II) phthalocyanine trisulfonate; zinc phthalocyanine trisulfonate; zinc (II) (t-butyl)$_3$-phthalocyanine diol; zinc tetradibenzobarreleno-octabutoxy-phthalocyanine; zinc (II) 2,9,16,23,-tetrakis-(3-(N-methyl)pyridyloxy)phthalocyanine tetraiodide; and zinc (II) 2,3,9,10,16,17,23,24-octakis-(3-(N-methyl)pyridyloxy)phthalocyanine complex octaiodide; and zinc (II) 2,3,9,10,16,17,23,24-octakis-(3-pyridyloxy)phthalocyanine.

Exemplary methylene blue derivatives include 1-methyl methylene blue; 1,9-dimethyl methylene blue; methylene blue; methylene blue (16 μM); methylene blue (14 μM); methylene violet; bromomethylene violet; 4-iodomethylene violet; 1,9-dimethyl-3-dimethyl-amino-7-diethyl-amino-phenothiazine; and 1,9-dimethyl-3-diethylamino-7-dibutyl-amino-phenothiazine.

Exemplary naphthalimides blue derivatives include N,N'-bis-(hydroperoxy-2-methoxyethyl)-1,4,5,8-naphthaldiimide; N-(hydroperoxy-2-methoxyethyl)-1,8-naphthalimide; 1,8-naphthalimide; N,N'-bis(2,2-dimethoxyethyl)-1,4,5,8-naphthaldiimide; and N,N'-bis(2,2-dimethylpropyl)-1,4,5,8-naphthaldiimide.

Exemplary naphthalocyanines include aluminum t-butylchloronaphthalocyanine; silicon bis(dimethyloctadecylsiloxy) 2,3-naphthalocyanine; silicon bis(dimethyloctadecylsiloxy) naphthalocyanine; silicon bis(dimethylthexylsiloxy) 2,3-naphthalocyanine; silicon bis(dimethylthexylsiloxy) naphthalocyanine; silicon bis(t-butyldimethylsiloxy) 2,3-naphthalocyanine; silicon bis(tert-butyldimethylsiloxy) naphthalocyanine; silicon bis(tri-n-hexylsiloxy) 2,3-naphthalocyanine; silicon bis(tri-n-hexylsiloxy) naphthalocyanine; silicon naphthalocyanine; t-butylnaphthalocyanine; zinc (II) naphthalocyanine; zinc (II) tetraacetyl-amidonaphthalocyanine; zinc (II) tetraaminonaphthalocyanine; zinc (II) tetrabenzamidonaphthalocyanine; zinc (II) tetrahexylamidonaphthalocyanine; zinc (II) tetramethoxy-benzamidonaphthalocyanine; zinc (II) tetramethoxynaphthalocyanine; zinc naphthalocyanine tetrasulfonate; and zinc (II) tetradodecylamidonaphthalocyanine.

Exemplary nile blue derivatives include benzo[a]phenothiazinium, 5-amino-9-diethylamino-; benzo[a]phenothiazinium, 5-amino-9-diethylamino-6-iodo-; benzo[a]phenothiazinium, 5-benzylamino-9-diethylamino-; benzo[a]phenoxazinium, 5-amino-6,8-dibromo-9-ethylamino-; benzo[a]phenoxazinium, 5-amino-6,8-diiodo-9-ethylamino-; benzo[a]phenoxazinium, 5-amino-6-bromo-9-diethylamino-; benzo[a]phenoxazinium, 5-amino-9-diethylamino-(nile blue A); benzo[a]phenoxazinium, 5-amino-9-diethylamino-2,6-diiodo-; benzo[a]phenoxazinium, 5-amino-9-diethylamino-2,-iodo; benzo[a]phenoxazinium, 5-amino-9-diethylamino-6-iodo-; benzo[a]phenoxazinium, 5-benzylamino-9-diethylamino-(nile blue 2B); 5-ethylamino-9-diethylamino-benzo[a]phenoselenazinium chloride; 5-ethylamino-9-diethyl-aminobenzo[a]phenothiazinium chloride; and 5-ethylamino-9-diethyl-aminobenzo[a]phenoxazinium chloride.

Exemplary NSAIDs (nonsteroidal anti-inflammatory drugs) include benoxaprofen; carprofen; carprofen dechlorinated (2-(2-carbazolyl) propionic acid); carprofen (3-chlorocarbazole); chlorobenoxaprofen; 2,4-dichlorobenoxaprofen; cinoxacin; ciprofloxacin; decarboxy-ketoprofen; decarboxy-suprofen; decarboxy-benoxaprofen; decarboxy-tiaprofenic acid; enoxacin; fleroxacin; fleroxacin-N-oxide; flumequine; indoprofen; ketoprofen; lomefloxacin; 2-methyl-4-oxo-2H-1,2-benzothiazine-1,1-dioxide; N-demethyl fleroxacin; nabumetone; nalidixic acid; naproxen; norfloxacin; ofloxacin; pefloxacin; pipemidic acid; piroxicam; suprofen; and tiaprofenic acid.

Exemplary perylenequinones include hypericins such as hypericin; hypericin monobasic sodium salt; di-aluminum hypericin; di-copper hypericin; gadolinium hypericin; terbium hypericin, hypocrellins such as acetoxy hypocrellin A; acetoxy hypocrellin B; acetoxy iso-hypocrellin A; acetoxy iso-hypocrellin B; 3,10-bis[2-(2-aminoethylamino)ethanol] hypocrellin B; 3,10-bis[2-(2-aminoethoxy)ethanol] hypocrellin B; 3,10-bis[4-(2-aminoethyl)morpholine] hypocrellin B; n-butylaminated hypocrellin B; 3,10-bis(butylamine) hypocrellin B; 4,9-bis(butylamine) hypocrellin B; -carboxylic acid hypocrellin B; cystamine-hypocrellin B; 5-chloro hypocrellin A or 8-chloro hypocrellin A; 5-chloro hypocrellin B or 8-chloro hypocrellin B; 8-chloro hypocrellin B; 8-chloro hypocrellin A or 5-chloro hypocrellin A; 8-chloro hypocrellin B or 5-chloro hypocrellin B; deacetylated aldehyde hypocrellin B; deacetylated hypocrellin B; deacetylated hypocrellin A; deacylated, aldehyde hypocrellin B; demethylated hypocrellin B; 5,8-dibromo hypocrellin A; 5,8-dibromo hypocrellin B; 5,8-dibromo iso-hypocrellin B; 5,8-dibromo [1,12-CBr=CMeCBr(COMe)] hypocrellin B; 5,8-dibromo[1,12-CHBrC(=CH$_2$)CBr(COMe)] hypocrellin B; 5,8-dibromo[1-CH$_2$COMe, 12-COCOCH$_2$Br—] hypocrellin B; 5,8-dichloro hypocrellin A; 5,8-dichloro hypocrellin B; 5,8-dichlorodeacytylated hypocrellin B; 5,8-diiodo hypocrellin A; 5,8-diiodo hypocrellin B; 5,8-diiodo [1,12-CH=CMeCH(COCH$_2$I$_2$)—] hypocrellin B; 5,8-diiodo[1,12-CH$_2$C(CH$_2$I)=C(COMe)—] hypocrellin B; 2-(N,N-diethylamino) ethylaminated hypocrellin B; 3,10-bis[2-(N,N-diethylamino)-ethylamine]hypocrellin B; 4,9-bis[2-(N,N-diethyl-amino)-ethylamine] iso-hypocrellin B; dihydro-1,4-thiazine carboxylic acid hypocrellin B; dihydro-1,4-thiazine hypocrellin B; 2-(N,N-dimethylamino)propylamine hypocrellin B; dimethyl-1,3,5,8,10,12-hexamethoxy-4,9-perylenequinone-6,7-diacetate; dimethyl-5,8-dihydroxy-1,3,10,13-tetramethoxy-4,9-perylenequinone-6,7-diacetate; 2,11-dione hypocrellin A; ethanolamine hypocrellin B; ethanolamine iso-hypocrellin B; ethylenediamine hypocrellin B; 11-hydroxy hypocrellin B or 2-hydroxy hypocrellin B; hypocrellin A; hypocrellin B; 5-iodo [1,12-CH$_2$C(CH$_2$I)=C(COMe)—] hypocrellin B; 8-iodo[1,12-CH$_2$C(CH$_2$I)=C(COMe)-] hypocrellin B; 9-methylamino iso-hypocrellin B; 3,10-bis[2-(N,N-methylamino)propylamine]hypocrellin B; 4,9-bis(methylamine iso-hypocrellin B; 14-methylamine iso-hypocrellin B; 4-methylamine iso-hypocrellin B; methoxy hypocrellin A; methoxy hypocrellin B; methoxy iso-hypocrellin A; methoxy iso-hypocrellin B; methylamine hypocrellin B; 2-morpholino ethylaminated hypocrellin B; pentaacetoxy hypocrellin A; PQP derivative; tetraacetoxy hypocrellin B; 5,8,15-tribromo hypocrellin B; calphostin C, Cercosporins such as acetoxy cercosporin; acetoxy iso-cercosporin; aminocercosporin; cercosporin; cercosporin+iso-cercosporin (1/1 molar); diaminocercosporin; dimethylcercosporin; 5,8-dithiophenol cercosporin; iso-cercosporin; methoxycercosporin; methoxy iso-cercosporin; methylcercosporin; noranhydrocercosporin; elsinochrome A; elsinochrome B; phleichrome; and rubellin A.

Exemplary phenols include 2-benzylphenol; 2,2'-dihydroxybiphenyl; 2,5-dihydroxybiphenyl; 2-hydroxybiphenyl; 2-methoxybiphenyl; and 4-hydroxybiphenyl.

Exemplary pheophorbides include pheophorbide a; methyl 13$^1$-deoxy-20-formyl-7,8-vic-dihydro-bacterio-meso-pheophorbide a; methyl-2-(1-dodecyloxyethyl)-2-devinyl-pyropheophorbide a; methyl-2-(1-heptyl-oxyethyl)-2-devinyl-pyropheophorbide a; methyl-2-(1-hexyl-oxyethyl)-2-devinyl-pyropheophorbide a; methyl-2-(1-methoxy-ethyl)-2-devinyl-pyropheophorbide a; methyl-2-(1-pentyl-oxyethyl)-2-devinyl-pyropheophorbide a; magnesium methyl bacteriopheophorbide d; methyl-bacteriopheophorbide d; and pheophorbide.

Exemplary pheophytins include bacteriopheophytin a; bacteriopheophytin b; bacteriopheophytin c; bacteriopheophytin d; 10-hydroxy pheophytin a; pheophytin; pheophytin a; and protopheophytin.

Exemplary photosensitizer dimers and conjugates include aluminum mono-(6-carboxy-pentyl-amino-sulfonyl)-trisulfophthalocyanine bovine serum albumin conjugate; dihematoporphyrin ether (ester); dihematoporphyrin ether; dihematoporphyrin ether (ester)-chlorin; hematoporphyrin-chlorin ester; hematoporphyrin-low density lipoprotein conjugate; hematoporphyrin-high density lipoprotein conjugate; porphine-2,7,18-tripropanoic acid, 13,13'-(1,3-propanediyl)bis[3,8,12,17-tetramethyl]-; porphine-2,7,18-tripropanoic acid, 13,13'-(1,11-undecanediyl)bis[3,8,12,17-tetramethyl]-; porphine-2,7,18-tripropanoic acid, 13,13'-(1,6-hexanediyl)bis[3,8,12,17-tetramethyl]-; SnCe6-MAb conjugate 1.7:1; SnCe6-MAb conjugate 1.7:1; SnCe6-MAb conjugate 6.8:1; SnCe6-MAb conjugate 11.2:1; SnCe6-MAb conjugate 18.9:1; SnCe6-dextran conjugate 0.9:1; SnCe6-dextran conjugate 3.5:1; SnCe6-dextran conjugate 5.5:1; SnCe6-dextran conjugate 9.9:1; α-terthienyl-bovine serum albumin conjugate (12:1); α-terthienyl-bovine serum albumin conjugate (4:1); and tetraphenylporphine linked to 7-chloroquinoline.

Exemplary phthalocyanines include (diol) (t-butyl)$_3$-phthalocyanine; (t-butyl)$_4$-phthalocyanine; cis-octabutoxy-dibenzo-dinaphtho-porphyrazine; trans-octabutoxy-dibenzo-dinaphtho-porphyrazine; 2,3,9,10,16,17,23,24-octakis2-ethoxyethoxy) phthalocyanine; 2,3,9,10,16,17,23,24-octakis(3,6-dioxaheptyloxy) phthalocyanine; octa-n-butoxy phthalocyanine; phthalocyanine; phthalocyanine sulfonate; phthalocyanine tetrasulphonate; phthalocyanine tetrasulfonate; t-butyl-phthalocyanine; tetra-t-butyl phthalocyanine; and tetradibenzobarreleno-octabutoxy-phthalocyanine.

Exemplary porphycenes include 2,3-($2^3$-carboxy-$2^4$-methoxycarbonyl benzo)-7,12,17-tris(2-methoxyethyl) porphycene; 2-(2-hydroxyethyl)-7,12,17-tri(2-methoxyethyl) porphycene; 2-(2-hydroxyethyl)-7,12,17-tri-n-propyl-porphycene; 2-(2-methoxyethyl)-7,12,17-tri-n-propyl-porphycene; 2,7,12,17-tetrakis(2-methoxyethyl) porphycene; 2,7,12,17-tetrakis(2-methoxyethyl)-9-hydroxy-porphycene; 2,7,12,17-tetrakis(2-methoxyethyl)-9-methoxy-porphycene; 2,7,12,17-tetrakis(2-methoxyethyl)-9-n-bexyloxy-porphycene; 2,7,12,17-tetrakis(2-methoxyethyl)-9-acetoxy-porphycene; 2,7,12,17-tetrakis(2-methoxyethyl)-9-caproyloxy-porphycene; 2,7,12,17-tetrakis(2-methoxyethyl)-9-pelargonyloxy-porphycene; 2,7,12,17-tetrakis(2-methoxyethyl)-9-stearoyloxy-porphycene; 2,7,12,17-tetrakis(2-methoxyethyl)-9-(N-t-butoxycarbonylglycinoxy)-porphycene; 2,7,12,17-tetrakis (2-methoxyethyl)-9-[4-(((β-apo-7-carotenyl)benzoyloxyl-porphycene; 2,7,12,17-tetrakis (2-methoxyethyl)-9-amino-porphycene; 2,7,12,17-tetrakis(2-methoxyethyl)-9-acetamido-porphycene; 2,7,12,17-tetrakis(2-methoxyethyl)-9-glutaramido-porphycene; 2,7,12,17-tetrakis(2-methoxyethyl)-9-(methyl-glutaramido)-porphycene; 2,7,12,17-tetrakis(2-methoxyethyl)-9-(glutarimido)-porphycene; 2,7,12,17-tetrakis(2-methoxyethyl)-3-(N,N-dimethylaminomethyl)-porphycene; 2,7,12,17-tetrakis(2-methoxyethyl)-3-(N,N-dimethyl aminomethyl)-porphycene hydrochloride; 2,7,12,17-tetrakis(2-ethoxyethyl)-porphycene; 2,7,12,17-tetra-n-propyl-porphycene; 2,7,12,17-tetra-n-propyl-9-hydroxy-porphycene; 2,7,12,17-tetra-n-propyl-9-methoxy-porphycene; 2,7,12,17-tetra-n-propyl-9-acetoxy porphycene; 2,7,12,17-tetra-n-propyl-9-(t-butyl glutaroxy)-porphycene; 2,7,12,17-tetra-n-propyl-9-(N-t-butoxycarbonylglycinoxy)-porphycene; 2,7,12,17-tetra-n-propyl-9-(4-N-t-butoxy-carbonyl-butyroxy)-porphycene; 2,7,12,17-tetra-n-propyl-9-amino-porphycene; 2,7,12,17-tetra-n-propyl-9-acetamido-porphycene; 2,7,12,17-tetra-n-propyl-9-glutaramido-porphycene; 2,7,12,17-tetra-n-propyl-9-(methyl glutamido)-porphycene; 2,7,12,17-tetra-n-propyl-3-(N,N-dimethylaminomethyl) porphycene; 2,7,12,17-tetra-n-propyl-9,10-benzo porphycene; 2,7,12,17-tetra-n-propyl-9-p-benzoyl carboxy-porphycene; 2,7,12,17-tetra-n-propyl-porphycene; 2,7,12,17-tetra-t-butyl-3,6; 13,16-dibenzo-porphycene; 2,7-bis(2-hydroxyethyl)-12,17-di-n-propyl-porphycene; 2,7-bis(2-methoxyethyl)-12,17-di-n-propyl-porphycene; and porphycene.

Exemplary porphyrins include 5-azaprotoporphyrin dimethylester; bis-porphyrin; coproporphyrin III; coproporphyrin III tetramethylester; deuteroporphyrin; deuteroporphyrin IX dimethylester; diformyldeuteroporphyrin IX dimethylester; dodecaphenylporphyrin; hematoporphyrin; hematoporphyrin (8 μM); hematoporphyrin (400 μM); hematoporphyrin (3 μM); hematoporphyrin (18 μM); hematoporphyrin (30 μM); hematoporphyrin (67 μM); hematoporphyrin (150 μM); hematoporphyrin IX; hematoporphyrin monomer; hematoporphyrin dimer; hematoporphyrin derivative; hematoporphyrin derivative (6 μM); hematoporphyrin derivative (200 μM); hematoporphyrin derivative A (20 μM); hematoporphyrin IX dihydrochloride; hematoporphyrin dihydrochloride; hematoporphyrin IX dimethylester; haematoporphyrin IX dimethylester; mesoporphyrin dimethylester; mesoporphyrin IX dimethylester; monoformyl-monovinyl-deuteroporphyrin IX dimethylester; monohydroxyethylvinyl deuteroporphyrin; 5,10,15,20-tetra(o-hydroxyphenyl) porphyrin; 5,10,15,20-tetra(m-hydroxyphenyl) porphyrin; 5,10,15,20-tetrakis-(m-hydroxyphenyl) porphyrin; 5,10,15,20-tetra(p-hydroxyphenyl) porphyrin; 5,10,15,20-tetrakis (3-methoxyphenyl) porphyrin; 5,10,15,20-tetrakis (3,4-dimethoxyphenyl) porphyrin; 5,10,15,20-tetrakis (3,5-dimethoxyphenyl) porphyrin; 5,10,15,20-tetrakis (3,4,5-trimethoxyphenyl) porphyrin; 2,3,7,8,12,13,17,18-octaethyl-5,10,15,20-tetraphenylporphyrin; Photofrin®; Photofrin® II; porphyrin c; protoporphyrin; protoporphyrin IX; protoporphyrin dimethylester; protoporphyrin IX dimethylester; protoporphyrin propylaminoethylformamide iodide; protoporphyrin N,N-dimethylaminopropylformamide; protoporphyrin propylaminopropylformamide iodide; protoporphyrin butylformamide; protoporphyrin N,N-dimethylaminoformamide; protoporphyrin formamide; sapphyrin 13,12,13,22-tetraethyl-2,7,18,23 tetramethyl sapphyrin-8,17-dipropanol; sapphyrin 23,12,13,22-tetraethyl-2,7,18,23 tetramethyl sapphyrin-8-monoglycoside; sapphyrin 3; meso-tetra-(4-N-carboxyphenyl)-porphine; tetra-(3-methoxyphenyl)-porphine; tetra-(3-methoxy-2,4-difluorophenyl)-porphine; 5,10,15,20-tetrakis(4-N-methylpyridyl) porphine; meso-tetra(4-N-methylpyridyl)-porphine tetrachloride; meso-tetra(4-N-methylpyridyl)-porphine; meso-tetra-(3-N-methylpyridyl)-porphine; meso-tetra-(2-N-methylpyridyl)-porphine; tetra(4-N,N,N-trimethylanilinium) porphine; meso-tetra-(4-N,N,N'''-trimethylaminophenyl) porphine tetrachloride; tetranaphthaloporphyrin; 5,10,15,20-tetraphenylporphyrin; tetraphenylporphyrin; meso-tetra-(4-N-sulfonatophenyl)-porphine; tetraphenylporphine tetrasulfonate; meso-tetra(4-sulfonatophenyl) porphine; tetra(4-sulfonatophenyl)porphine; tetraphenylporphyrin sulfonate; meso-tetra(4-sulfonatophenyl)porphine; tetrakis (4-sulfonatophenyl)porphyrin; meso-tetra(4-sulfonatophenyl)porphine; meso(4-sulfonatophenyl)porphine; meso-tetra(4-sulfonatophenyl)porphine; tetrakis(4-sulfonatophenyl)porphyrin; meso-tetra(4-N-trimethylanilinium)-porphine; uroporphyrin; uroporphyrin I (17 μM); uroporphyrin IX; and uroporphyrin I (18 μM).

Exemplary psoralens include psoralen; 5-methoxypsoralen; 8-methoxypsoralen; 5,8-dimethoxypsoralen; 3-carbethoxypsoralen; 3-carbethoxy-pseudopsoralen; 8-hydroxypsoralen; pseudopsoralen; 4,5',8-trimethylpsoralen; allopsoralen; 3-aceto-allopsoralen; 4,7-dimethyl-allopsoralen; 4,7,4'-trimethyl-allopsoralen; 4,7,5'-trimethyl-allopsoralen; isopseudopsoralen; 3-acetoisopseudopsoralen; 4,5'- dimethyl-isopseudopsoralen; 5',7-dimethyl-isopseudopsoralen; pseudoisopsoralen; 3-acetopseudoisopsoralen; 3,4',5'-trimethyl-aza-psoralen; 4,4',8-trimethyl-5'-amino-methylpsoralen; 4,4',8-trimethyl-phthalamyl-psoralen; 4,5',8-trimethyl-4'-aminomethyl psoralen; 4,5',8-trimethyl-bromopsoralen; 5-nitro-8-methoxy-psoralen; 5'-acetyl-4,8-dimethyl-psoralen; 5'-aceto-8-methyl-psoralen; and 5'-aceto-4,8-dimethyl-psoralen.

Exemplary purpurins include octaethylpurpurin; octaethylpurpurin zinc; oxidized octaethylpurpurin; reduced octaethylpurpurin; reduced octaethylpurpurin tin; purpurin 18; purpurin-18; purpurin-18-methyl ester; purpurin; tin ethyl etiopurpurin I; Zn(II) aetio-purpurin ethyl ester; and zinc etiopurpurin.

Exemplary quinones include 1-amino-4,5-dimethoxy anthraquinone; 1,5-diamino-4,8-dimethoxy anthraquinone; 1,8-diamino-4,5-dimethoxy anthraquinone; 2,5-diamino-1,8-dihydroxy anthraquinone; 2,7-diamino-1,8-dihydroxy anthraquinone; 4,5-diamino-1,8-dihydroxy anthraquinone; mono-methylated 4,5- or 2,7-diamino-1,8-dihydroxy anthraquinone; anthralin (keto form); anthralin; anthralin anion; 1,8-dihydroxy anthraquinone; 1,8-dihydroxy anthraquinone (Chrysazin); 1,2-dihydroxy anthraquinone; 1,2-dihydroxy anthraquinone (Alizarin); 1,4-dihydroxy anthraquinone (Quinizarin); 2,6-dihydroxy anthraquinone; 2,6-dihydroxy anthraquinone (Anthraflavin); 1-hydroxy anthraquinone (Erythroxy-anthraquinone); 2-hydroxy-anthraquinone; 1,2,5,8-tetra-hydroxy anthraquinone (Quinalizarin); 3-methyl-1,6,8-trihydroxy anthraquinone (Emodin); anthraquinone; anthraquinone-2-sulfonic acid; benzoquinone; tetramethyl benzoquinone; hydroquinone; chloro-hydroquinone; resorcinol; and 4-chlororesorcinol.

Exemplary retinoids include all-trans retinal; $C_{17}$ aldehyde; $C_{22}$ aldehyde; 11-cis retinal; 13-cis retinal; retinal; and retinal palmitate.

Exemplary rhodamines include 4,5-dibromo-rhodamine methyl ester; 4,5-dibromo-rhodamine n-butyl ester; rhodamine 101 methyl ester; rhodamine 123; rhodamine 6G; rhodamine 6G hexyl ester; tetrabromo-rhodamine 123; and tetramethyl-rhodamine ethyl ester.

Exemplary thiophenes include terthiophenes such as 2,2':5',2"-terthiophene; 2,2':5',2"-terthiophene-5-carboxamide; 2,2':5',2"-terthiophene-5-carboxylic acid; 2,2':5',2"-terthiophene-5-L-serine ethyl ester; 2,2':5',2"-terthiophene-5-N-isopropynyl-formamide; 5-acetoxymethyl-2,2':5',2"-terthiophene; 5-benzyl-2,2':5',2"-terthiophene-sulphide; 5-benzyl-2,2':5',2"-terthiophene-sulfoxide; 5-benzyl-2,2':5',2"-terthiophene-sulphone; 5-bromo-2,2':5',2"-terthiophene; 5-(butynyl-3'''-hydroxy)-2,2':5',2"-terthiophene; 5-carboxyl-5"-trimethylsilyl-2,2':5',2"-terthiophene; 5-cyano-2,2':5',2"-terthiophene; 5,5"-dibromo-2,2':5',2"-terthiophene; 5-(1''',1'''-dibromoethenyl)-2,2':5',2"-terthiophene; 5,5"-dicyano-2,2':5',2"-terthiophene; 5,5"-diformyl-2,2':5',2"-terthiophene; 5-difluoromethyl-2,2':5',2"-terthiophene; 5,5"-diiodo-2,2':5',2"terthiophene; 3,3"-dimethyl-2,2':5',2"-terthiophene; 5,5"-dimethyl-2,2':5',2"-terthiophene; 5-(3''',3'''-dimethylacryloyloxymethyl)-2,2':5',2"-terthiophene; 5,5"-di-(t-butyl)-2,2':5',2"-terthiophene; 5,5"-dithiomethyl-2,2':5',2"-terthiophene; 3'-ethoxy-2,2':5',2"-terthiophene; ethyl 2,2':5',2"-terthiophene-5-carboxylic acid; 5-formyl-2,2':5',2"-terthiophene; 5-hydroxyethyl-2,2':5',2"-terthiophene; 5-hydroxymethyl-2,2':5',2"-terthiophene; 5-iodo-2,2':5',2"-terthiophene; 5-methoxy-2,2':5',2"-terthiophene; 3'-methoxy-2,2':5',2"-terthiophene; 5-methyl-2,2':5',2"-terthiophene; 5-(3'''-methyl-2'''-butenyl)-2,2':5',2"-terthiophene; methyl 2,2':5',2"-terthiophene-5-[3'''-acrylate]; methyl 2,2':5',2"-terthiophene-5-(3'''-propionate); N-allyl-2,2':5',2"-terthiophene-5-sulphonamide; N-benzyl-2,2':5',2"-terthiophene-5-sulphonamide; N-butyl-2,2':5',2"-terthiophene-5-sulphonamide; N,N-diethyl-2,2':5',2"-terthiophene-5-sulphonamide; 3,3',4',3"-tetramethyl-2,2':5',2"-terthiophene; 5-t-butyl-5"-trimethylsilyl-2,2':5',2"-terthiophene; 3'-thiomethyl-2,2':5',2"-terthiophene; 5-thiomethyl-2,2':5',2"-terthiophene; 5-trimethylsilyl-2,2':5',2"-terthiophene, bithiophenes such as 2,2'-bithiophene; 5-cyano-2,2'-bithiophene; 5-formyl-2,2'-bithiophene; 5-phenyl-2,2'-bithiophene; 5-(propynyl)-2,2'-bithiophene; 5-(hexynyl)-2,2'-bithiophene; 5-(octynyl)-2,2'-bithiophene; 5-(butynyl-4"-hydroxy)-2,2'-bithiophene; 5-(pentynyl-5"-hydroxy)-2,2'-bithiophene; 5-(3",4"-dihydroxybutynyl)-2,2'-bithiophene derivative; 5-(ethoxybutynyl)-2,2'-bithiophene derivative, and misclaneous thiophenes such as 2,5-diphenylthiophene; 2,5-di(2-thienyl)furan; pyridine, 2,6-bis(2-thienyl)-; pyridine, 2,6-bis(thienyl)-; thiophene, 2-(1-naphthalenyl)-; thiophene, 2-(2-naphthalenyl)-; thiophene, 2,2'-(1,2-phenylene)bis-; thiophene, 2,2'-(1,3-phenylene)bis-; thiophene, 2,2'-(1,4-phenylene)bis-; 2,2':5',2":5",2'''-quaterthiophene; α-quaterthienyl; α-tetrathiophene; α-pentathiophene; α-hexathiophene; and α-heptathiophene.

Exemplary verdins include copro (II) verdin trimethyl ester; deuteroverdin methyl ester; mesoverdin methyl ester; and zinc methyl pyroverdin.

Exemplary vitamins include ergosterol (provitamin D2); hexamethyl-Co a Co b-dicyano-7-de(carboxymethyl)-7,8-didehydro-cobyrinate (Pyrocobester); pyrocobester; and vitamin D3.

Exemplary xanthene dyes include Eosin B (4',5'-dibromo, 2',7'-dinitro-fluorescein, dianion); eosin Y; eosin Y (2',4',5',7'-tetrabromo-fluorescein, dianion); eosin (2',4',5',7'-tetrabromo-fluorescein, dianion); eosin (2',4',5',7'-tetrabromo-fluorescein, dianion) methyl ester; eosin (2',4',5',7'-tetrabromo-fluorescein, monoanion) p-isopropylbenzyl ester; eosin derivative (2',7'-dibromo-fluorescein, dianion); eosin derivative (4',5'-dibromo-fluorescein, dianion); eosin derivative (2',7'-dichloro-fluorescein, dianion); eosin derivative (4',5'-dichloro-fluorescein, dianion); eosin derivative (2',7'-diiodo-fluorescein, dianion); eosin derivative (4',5'-diiodo-fluorescein, dianion); eosin derivative (tribromo-fluorescein, dianion); eosin derivative (2',4',5',7'-tetrachloro-fluorescein, dianion); eosin; eosin dicetylpyridinium chloride ion pair; erythrosin B (2',4',5',7'-tetraiodo-fluorescein, dianion); erythrosin; erythrosin dianion; erythrosin B; fluorescein; fluorescein dianion; phloxin B (2',4',5',7'-tetrabromo-3,4,5,6-tetrachloro-fluorescein, dianion); phloxin B (tetrachloro-tetrabromo-fluorescein); phloxine B; rose bengal (3,4,5,6-tetrachloro-2',4',5',7'-tetraiodofluorescein, dianion); rose bengal; rose bengal dianion; rose bengal O-methyl-methylester; rose bengal 6'-O-acetyl ethyl ester; rose bengal benzyl ester diphenyl-diiodonium salt; rose bengal benzyl ester triethylammonium salt; rose bengal benzyl ester, 2,4,6,-triphenylpyrilium salt; rose bengal benzyl ester, benzyltriphenyl-phosphonium salt; rose bengal benzyl ester, benzyltriphenyl phosphonium salt; rose bengal benzyl ester, diphenyl-iodonium salt; rose bengal benzyl ester, diphenyl-methylsulfonium salt; rose bengal benzyl ester, diphenyl-methyl-sulfonium salt; rose bengal benzyl ester, triethyl-ammonium salt; rose bengal benzyl ester, triphenyl pyrilium; rose bengal bis (triethyl-ammonium) salt) (3,4,5,6-tetrachloro-2',4',5',7'-tetraiodofluorescein, bis (triethyl-ammonium salt); rose bengal bis (triethyl-ammonium) salt; rose bengal bis(benzyl-triphenyl-phosphonium) salt (3,4,5,6-tetrachloro-2',4',5',7'-tetraiodofluorescein, bis(benzyl-triphenyl-phosphonium) salt); rose bengal bis(diphenyl-iodonium) salt (3,4,5,6-tetrachloro-2',4',5',7'-tetraiodofluorescein, bis(diphenyl-iodonium) salt); rose bengal dicetyl-pyridinium chloride ion pair; rose bengal ethyl ester triethyl ammonium salt; rose bengal ethyl ester triethyl ammonium salt; rose bengal ethyl ester; rose bengal methyl ester; rose bengal octyl ester tri-n-butyl-ammonium salt RB; rose bengal, 6'-O-acetyl-, and ethyl ester.

Any of the photoactive compounds described above can be used in the methods of the invention; of course, mixtures of two or more photoactive compounds can also be used; however, the effectiveness of the treatment depends on the absorption of light by the photoactive compound so that if mixtures are used in combination with light of a limited range of wavelengths, compounds with similar absorption maxima are preferred. Alternatively, and if the invention is practiced with light of a broader range of wavelengths or of discrete (or non-overlapping wavelengths), combinations of photoactive compounds with absorption spectra corresponding to wavelengths within the broader range or within the wavelengths present may be used.

In applications of the present invention to the treatment of ocular neovasculature (such as that of the cornea, iris, retina), the photoactive agent is formulated so as to provide an effective concentration to the target ocular tissue. The photoactive agent may be coupled to a specific binding ligand which may bind to a specific surface component of the target ocular tissue or, if desired, by formulation with a carrier that delivers higher concentrations to the target tissue.

The nature of the formulation will depend in part on the mode of administration and on the nature of the photoactive agent selected. To prepare a pharmaceutical formulation or composition comprising a PS of the invention, any pharmaceutically acceptable excipient, or combination thereof, appropriate to the particular photoactive compound may be used. Thus, the photoactive compound may be administered as an aqueous composition, as a transmucosal or transdermal composition, or in an oral formulation. The formulation may also include liposomes. Liposomal compositions are particularly preferred especially where the photoactive agent is a green porphyrin. Liposomal formulations are believed to deliver the green porphyrin selectively to the low-density lipoprotein component of plasma which, in turn acts as a carrier to deliver the active ingredient more effectively to the desired site. Increased numbers of LDL receptors have been shown to be associated with neovascularization, and by increasing the partitioning of the green porphyrin into the lipoprotein phase of the blood, it appears to be delivered more efficiently to neovasculature.

As previously mentioned, the method of the invention is particularly effective where the loss of visual acuity in the patient is associated with unwanted neovasculature. Green porphyrins, and in particular BPD-MA, strongly interact with such lipoproteins. LDL itself can be used as a carrier, but LDL is considerably more expensive and less practical than a liposomal formulation. LDL, or preferably liposomes, are thus preferred carriers for the green porphyrins since green porphyrins strongly interact with lipoproteins and are easily packaged in liposomes. Compositions of green porphyrins involving lipocomplexes, including liposomes, are described in U.S. Pat. No. 5,214,036 and in U.S. Pat. No. 6,074,666, the disclosures of both of these being incorporated herein by reference. Liposomal BPD-MA for intravenous administration can also be obtained from QLT Inc., Vancouver, British Columbia.

The photoactive compound can be administered in any of a wide variety of ways, for example, orally, parenterally, or rectally, or the compound may be placed directly in the eye. Parenteral administration, such as intravenous, intramuscular, or subcutaneous, is preferred. Intravenous injection or infusion are especially preferred. Localized administration, including topical administration, may also be used.

The dose of photoactive compound can vary widely depending on the mode of administration; the formulation in which it is carried, such as in the form of liposomes; or whether it is coupled to a target-specific ligand, such as an antibody or an immunologically active fragment. As is generally recognized, there is a nexus between the type of photoactive agent, the formulation, the mode of administration, and the dosage level. Adjustment of these parameters to fit a particular combination is possible.

While various photoactive compounds require different dosage ranges, if green porphyrins are used, a typical dosage is of the range of 0.1–50 mg/M$^2$ (of body surface area) preferably from about 1–10 mg/M$^2$ and even more preferably about 2–8 mg/M$^2$, and most preferably about 6 mg/M$^2$. However, these values are merely suggestions and may not apply to all photosensitizers. 6 mg/m$^2$ is approximately 0.15 mg/kg.

Systemic administration can also be stated in terms of amount of PS to body weight of the subject being treated. Dosages for this invention stated in such terms are less than about 10 µg/kg to 100 mg/kg body weight, preferably less than about 10 mg/kg, more preferably about 0.15 mg/kg in humans. Preferably, the PS is infused into a subject over a short period, such as, but not limited to, about 5 to about 120 minutes, about 10 to about 90 minutes, about 20 to about 60 minutes, or about 30 to 45 minutes. Particularly preferred is an infusion over 10 minutes.

The various parameters used for effective, selective photodynamic therapy in the invention are interrelated. Therefore, the dose should also be adjusted with respect to other parameters, for example, fluence, irradiance, duration of the light used in photodynamic therapy, and time interval between administration of the dose and the therapeutic irradiation. All of these parameters should be adjusted to produce significant enhancement of visual acuity without significant damage to the eye tissue.

Stated in alternative terms, as the photoactive compound dose is reduced, the fluence required to close choroidal neovascular tissue tends to increase. After the photoactive compound has been administered, the target ocular tissue is irradiated at the wavelength absorbed by the agent selected. The spectra for the photoactive compounds described above are known in the art; for any particular photoactive compound, it is a trivial matter to ascertain the spectrum. For green porphyrins, however, the desired wavelength range is generally between about 550 and 695 nm. A wavelength in this range is especially preferred for enhanced penetration into bodily tissues. Preferred wavelengths for the practice of the invention are at about 685–695 nm, particularly at about 686, about 687, about 688, about 689, about 690, about 691, and about 692 nm.

PS spectra, as well as wavelengths for PS activation, have been described in the art. Irradiation of the administered PS is preferably at the wavelength absorbed by the PS selected. For any particular PS, it is a trivial matter to ascertain the spectrum.

As a result of being irradiated, the photoactive compound in its excited state is thought to interact with other compounds to form reactive intermediates, such as singlet oxygen, which can cause disruption of cellular structures. Possible cellular targets include the cell membrane, mitochondria, lysosomal membranes, and the nucleus. Evidence from tumor and neovascular models indicates that occlusion of the vasculature is a major mechanism of photodynamic therapy, which occurs by damage to endothelial cells, with subsequent platelet adhesion, degranulation, and thrombus formation.

The fluence during the irradiating treatment can vary widely, depending on type of tissue, depth of target tissue, and the amount of overlying fluid or blood, but preferably varies from about 20–200 Joules/cm$^2$. The irradiation levels will be in the range generally employed for PDT treatment of CNV as known in the art. Typical levels for the practice of the invention are in the range of about 12.5, 25, 50, 75, and 100 J/cm$^2$. The radiation can be supplied by any convenient source using a wavelength absorbed by the photosensitizer used. Examples of sources for use in the present methods include any assembly capable of producing visible light.

The irradiance typically varies from about 150–900 mW/cm$^2$, with the range between about 150–600 mW/cm$^2$ being preferred. Preferred rates for use with green porphyrins or BPDs is from about 200 to 250, about 250 to 300, about 300 to 350, about 350 to 400, about 400 to 450, about 450 to 500, and about 500 to 550 mW/cm$^2$.

The optimum time following photoactive agent administration until light treatment can also vary widely depending on the mode of administration, the form of administration and the specific ocular tissue being targeted. Typical times after administration of the photoactive agent range from about 1 minute to about 3 hours, preferably about 5–30 minutes, and more preferably about 10–25 minutes. Particularly preferred is irradiation at 15 minutes after the start of PS infusion. The incubation before irradiation may occur in the dark or low-level light may be supplied during PS administration.

The duration of light irradiation depends on the fluence desired; for an irradiance of 600 mW/cm$^2$ a fluence of 50 J/cm$^2$ requires 83 seconds of irradiation; 150 J/cm$^2$ requires 249 seconds of irradiation.

Clinical examination and fundus photography typically reveal no color change immediately following photodynamic therapy, although a mild retinal whitening occurs in some cases after about 24 hours. In general, effects of the photodynamic therapy as regards reduction of neovascularization can be performed using standard fluorescein angiographic techniques at specified periods after treatment. Parameters that are monitored in AMD patients include the progression from baseline of classic CNV in the lesion, progression from baseline of occult CNV in the lesion, change from baseline in greatest linear dimension of the entire CNV lesion, change from baseline in area of the entire lesion including CNV, natural scar and obscuring features (measured in Macular Photocoagulation disc area, MPS DA, see Macular Photocoagulation Study Group, Subfoveal neovascular lesions in age-related macular degeneration: guidelines for evaluation and treatment in the Macular Photocoagulation Study. Arch. Ophthalmol. 1991; 109: 1242–1257), and change from baseline in area of the entire lesion plus surrounding atrophy (measured in MPS DA).

Visual acuity is monitored using means standard in the art and conventional "eye charts" in which visual acuity is evaluated by the ability to discern letters of a certain size, usually with five letters on a line of given size. Measures of visual acuity are known in the art and standard means are used to evaluate visual acuity according to the present invention. Particularly preferred for evaluation of visual acuity are the ETDRS charts mentioned in the reference by the Macular Photocoagulation Study, mentioned above. Parameters that are typically monitored in evaluation of a treatment protocol are gain or loss of letters from baseline (e.g. percent of patients gaining/losing 15 letters or more, percent of patients losing 30 letters or more, best-corrected visual acuity decreasing less than 34 letters, etc.), the time it takes to lose letters (e.g. time to lose 15 or more letters, time to lose 30 or more letters) and absolute changes from baseline visual acuity scores.

After the initial PDT treatment, treatment is repeated at least twice before the examination at approximately 6 months post initial treatment and any treatment that follows this evaluation. For example, subsequent treatments can be carried out at monthly intervals, providing a total of 5 treatments, carried out at 1, 2, 3, 4 and 5 months, during the first 6 months following the initial treatment. Two, three, four, five, or more than five evaluations and/or re-treatments may be conducted during the initial six month period.

Preferably, treatments are carried out at one and one half monthly intervals (or approximately 6–7 week intervals), providing a total of 3 treatments during the initial 6 month period, at 1.5, 3 and 4.5 months after initial treatment. Alternatively treatments can be spaced at irregular intervals, if upon angiographic evaluation, it becomes apparent that neovascular leakage is occurring. For example, a treatment might be given at 1.5 months, another at 2.5 months and another at 4 months, if necessary. The treatments conducted during the six months following an initial treatment may also be characterized as treatments at an increased frequency in comparison to the established protocol of treatment at three month intervals. The frequency may be described as being at least about every 60 days, at least about every 45 days, at least about every 30 days, or at least about every 15 days following an initial treatment and for the duration of about six months.

The following example is to illustrate but not to limit the invention.

EXAMPLE 1

Effect of Early Frequent Re-Treatment on the Loss of Visual Acuity

Patients who have been identified as having predominantly classic subfoveal CNV due to AMD are selected. Generally the patients have a lesions size with a greatest linear dimension less than or equal to 5400 μm, and with a visual acuity score in the range of 73–34 letters as assessed on ETDRS chart. The patients are divided into two groups Group 1: Standard regimen and Group 2: Early Frequent Re-treatment regimen. Both Groups 1 and Group 2 receive a first verteporfin PDT treatment as follows:

A 15 mg-vial of liposomally-formulated verteporfin (Verteporfin for Injection (Visudyne™) is reconstituted with 7 mL of sterile water for injection to provide 7.5 mL containing a final concentration of 2 mg/mL. The volume of reconstituted drug required to achieve a dose of 6 mg/M$^2$ (based upon the height and weight of the patient, calculated from a nomogram) is withdrawn from the vial and diluted with 5% dextrose for injection to make a total infusion volume of 30 mL. The full infusion volume is administered intravenously over 10 minutes using an appropriate syringe pump and in-line filter. Fifteen minutes after the start of the infusion, light is administered to the lesion from a diode laser through a fiber optic delivered via a slit lamp, and utilizing a suitable lens. A light dose of 50J/cm$^2$ is applied at a fluency rate of 600 mW/cm$^2$. 50 J/cm$^2$ (83 second exposure).

Patients are assessed for visual acuity and CNV lesions are evaluated by fluorescein angiography every 1.5 months for the first 6 months, and every three months thereafter. If the angiograph indicates CNV leakage, the patients are given either a treatment identical to the first treatment (Group 2), or a placebo treatment (Group 1), which is identical to the first treatment in all respects except that the 30-ml infusion contains no Verteporfin for Injection. (Light is administered to the placebo group.) If the angiograph does not indicate CNV leakage, no treatment is given following evaluation. The follow-up treatments are given in accordance with the following schedule, if CNV leakage has occurred.

| Months after first treatment | Group 1 Standard Regimen | Group 2 Early Frequent Re-treatment Regimen |
| --- | --- | --- |
| 1.5 (+ or − 1 week) | Placebo | Verteporfin for Injection |
| 3.0 (+ or − 1 week) | Verteporfin for Injection | Verteporfin for Injection |
| 4.5 (+ or − 1 week) | Placebo | Verteporfin for Injection |
| 6.0 (+ or − 1 week) | Verteporfin for Injection | Verteporfin for Injection |
| 9.0, 12.0, 15.0, 18.0 and 21.0 (+ or − 2 weeks) | Verteporfin for Injection | Verteporfin for Injection |

Twenty four months after the initial treatment, all patients are evaluated for visual acuity, and visual acuity is compared between Groups 1 and 2. Group 2 patients have lost less visual acuity than Group 1 patients.

All references cited herein are hereby incorporated by reference in their entireties, whether previously specifically incorporated or not. As used herein, the terms "a", "an", and "any" are each intended to include both the singular and plural forms.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

The invention claimed is:

1. A method of improving photodynamic therapy (PDT) mediated treatment of choroidal neovasculature in a subject comprising
providing, during a period of about three months following an initial PDT treatment, at least two additional PDT treatments to said subject after evaluations for neovascular leakage at about 45 days and about 90 days following said initial PDT treatment.

2. A method of improving photodynamic therapy (PDT) mediated treatment of choroidal neovasculature in a subject comprising
providing, during a period of about three months following an initial PDT treatment, a total of at least three additional PDT treatments following said initial PDT treatment.

3. The method of claim 2 wherein a total of three additional PDT treatments are provided at about 30 days, at about 60 days and at about 90 days following said initial PDT treatment.

4. The method of claim 2 wherein a total of at least three additional PDT treatments are provided at about 15 days, at about 30 days, at about 45 days, at about 60 days, at about 75 days and at about 90 days following said initial PDT treatment.

5. A method of improving photodynamic therapy (PDT) mediated treatment of choroidal neovasculature in a subject comprising providing, during a period of about six months following an initial PDT treatment, additional PDT treatments to said subject after evaluations for neovascular leakage at intervals of about 60 days.

6. The method of claim 1, 2, or 5, wherein the CNV is in a subject afflicted or diagnosed with age-related macular degeneration (AMD).

7. The method of claim 6, wherein the AMD is the "wet" form.

8. The method of claim 1, 2, or 5, wherein said additional PDT treatments comprise the administration of a photosensitizer (PS).

9. The method of claim 8, wherein the PS is administered at a concentration ranging between about 2 to 8 mg PS per square meter of body surface area of said subject.

10. The method of claim 9, wherein the PS is administered at a concentration of 6 mg PS per square meter of body surface are of said subject.

11. The method of claim 8, wherein the PS is a green porphyrin.

12. The method of claim 11, wherein the green porphyrin is selected from a group consisting of BPD-DA, BPD-DB, BPD-MA, BPD-MB, EA6, and B3.

13. The method of claim 12, wherein the green porphyrin is BPD-MA.

14. The method of claim 11, wherein the PS is coupled to a specific binding ligand.

15. The method of claim 8, wherein the PS is formulated with a carrier.

16. The method of claim 15, wherein the formulation is selected from the group consisting of a liposome, emulsion, or aqueous solution.

17. The method of claim 1, 2, or 5, wherein said additional PDT treatments comprise irradiation with electromagnetic radiation containing wavelengths in the visible light spectra.

18. The method of claim 17, wherein the irradiation provides between 12.5 J/cm$^2$ and 100 J/cm$^2$.

19. The method of claim 17, wherein said irradiating occurs between 5 to 30 minutes after administration of a photosensitizer.

20. A method of improving photodynamic therapy (PDT) mediated treatment of choroidal neovasculature in a subject comprising providing, during a period of about six months following an initial PDT treatment, a total of at least three additional PDT treatments following said initial PDT treatment to said subject after evaluation for neovascular leakage.

21. The method of claim 20, wherein the total of three additional treatments are provided at about 45 days, at about 90 days, and at about 135 days following said initial PDT treatment.

22. The method of claim 20, further comprising providing, during a period of about six months following the initial PDT treatment, a total of five additional PDT treatments following said initial PDT treatment to said subject after evaluations for neovascular leakage.

23. The method of claim 22, wherein the total of five additional treatments are provided at about 30 days, at about 60 days, at about 90 days, at about 120 days, and at about 150 days following said initial PDT treatment.

* * * * *